(12) United States Patent
Zavaleta et al.

(10) Patent No.: US 10,371,642 B2
(45) Date of Patent: Aug. 6, 2019

(54) RAMAN TOPOGRAPHY SYSTEM AND METHODS OF IMAGING

(71) Applicant: The Board of Trustees of the Leland Stanford Junior University, Palo Alto, CA (US)

(72) Inventors: Cristina Zavaleta, Los Angeles, CA (US); Michael J. Mandella, Palo Alto, CA (US); Zhen Qiu, Okemos, MI (US)

( * ) Notice: Subject to any disclaimer, the term of this patent is extended or adjusted under 35 U.S.C. 154(b) by 0 days.

(21) Appl. No.: 15/835,582

(22) Filed: Dec. 8, 2017

(65) Prior Publication Data

US 2018/0164217 A1 Jun. 14, 2018

Related U.S. Application Data

(60) Provisional application No. 62/431,492, filed on Dec. 8, 2016.

(51) Int. Cl.
| | |
|---|---|
| *G01J 3/44* | (2006.01) |
| *G01N 21/65* | (2006.01) |
| *A61B 5/00* | (2006.01) |
| *A61B 5/15* | (2006.01) |
| *A61K 49/00* | (2006.01) |
| *G01N 21/64* | (2006.01) |
| *A61B 1/04* | (2006.01) |
| *A61B 5/107* | (2006.01) |

(52) U.S. Cl.
CPC ............. *G01N 21/65* (2013.01); *A61B 1/043* (2013.01); *A61B 5/0071* (2013.01); *A61B 5/0075* (2013.01); *A61B 5/0084* (2013.01); *A61B 5/1072* (2013.01); *A61B 5/15* (2013.01); *A61B 5/150832* (2013.01); *A61K 49/0002* (2013.01); *G01N 21/6456* (2013.01); *G01N 21/658* (2013.01); *A61B 2562/0257* (2013.01); *G01N 2021/6439* (2013.01); *G01N 2021/656* (2013.01)

(58) Field of Classification Search
CPC ........ G01J 3/44; G01J 3/02; G01N 2021/656; G01N 21/65; G01N 21/658
USPC .......................................................... 356/301
See application file for complete search history.

(56) References Cited

U.S. PATENT DOCUMENTS

| | | | | |
|---|---|---|---|---|
| 2006/0119853 A1* | 6/2006 | Baumberg | ........... | G01N 21/658 356/445 |
| 2010/0069760 A1* | 3/2010 | Tang | ................... | A61B 5/0075 600/478 |
| 2012/0123205 A1* | 5/2012 | Nie | .................... | A61B 1/00174 600/109 |
| 2012/0179029 A1* | 7/2012 | Kircher | ................ | A61B 5/0042 600/421 |
| 2012/0327417 A1* | 12/2012 | Amako | ................ | G01N 21/658 356/445 |
| 2013/0176562 A1* | 7/2013 | Shioi | ..................... | G01J 3/4412 356/301 |
| 2014/0226157 A1* | 8/2014 | Dogariu | .................... | G01J 3/44 356/301 |
| 2014/0310839 A1* | 10/2014 | Wickramasinghe | ... | G01Q 30/02 850/40 |

(Continued)

*Primary Examiner* — Md M Rahman
(74) *Attorney, Agent, or Firm* — Thomas|Horstemeyer, LLP

(57) ABSTRACT

The present disclosure describes a Raman topography system, which includes a container with at least one Raman probe positioned within. Also described are methods of imaging which include the Raman topography system.

24 Claims, 4 Drawing Sheets

(56) References Cited

U.S. PATENT DOCUMENTS

| | | | | |
|---|---|---|---|---|
| 2014/0316255 | A1* | 10/2014 | Garai | G01J 1/0433 600/424 |
| 2014/0358447 | A1* | 12/2014 | Doyle | A61B 8/085 702/19 |
| 2015/0335248 | A1* | 11/2015 | Huang | G01N 21/65 600/476 |
| 2015/0377787 | A1* | 12/2015 | Zeng | G01N 21/64 356/301 |
| 2017/0303830 | A1* | 10/2017 | Klein | A61B 5/0059 |

* cited by examiner

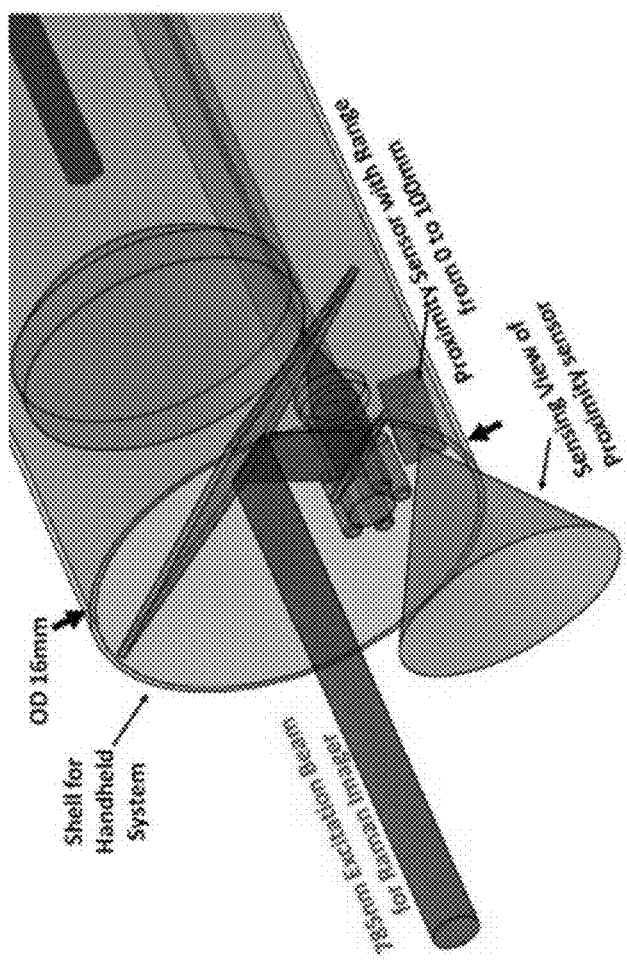
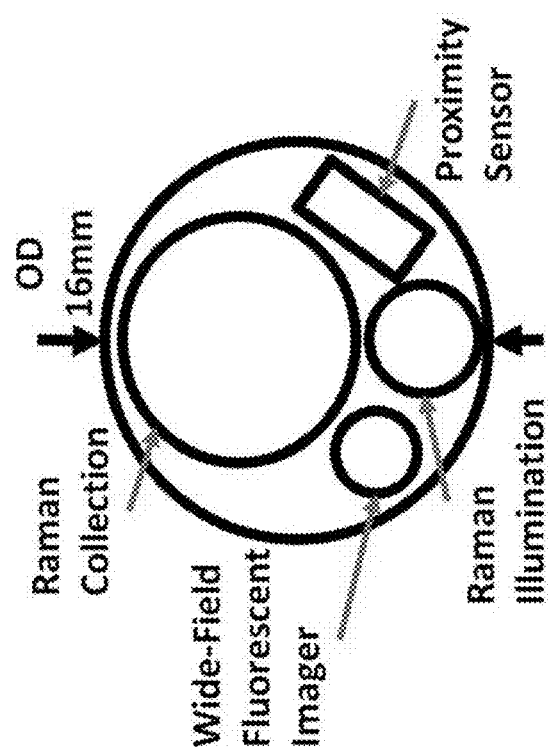
Fig. 3B
Fig. 3A

RAMAN TOPOGRAPHY SYSTEM AND METHODS OF IMAGING

CROSS-REFERENCE TO RELATED APPLICATIONS

This application claims the benefit of and priority to U.S. Provisional Application Ser. No. 62/431,492, having the title "RAMAN TOPOGRAPHY SYSTEM AND METHODS OF IMAGING", filed on Dec. 8, 2016, the disclosure of which is incorporated herein by reference in its entirety.

STATEMENT REGARDING FEDERALLY SPONSORED RESEARCH OR DEVELOPMENT

This invention was made with Government support under contracts CA160834 and CA184608 awarded by the National Institutes of Health. The Government has certain rights in the invention.

BACKGROUND

One of the biggest challenges that surgical oncologists face in the operating room (OR) is determining where the tumor they are resecting begins and ends. Obtaining negative tumor margins can be essential to the patient's survival. However, the tools available to surgeons during the actual resection are limited to non-existent. As a result, positive tumor margins are often left which can lead to another expensive trip to the OR for re-excision along with more imaging and pathology costs.

SUMMARY

The present disclosure describes a Raman topography system, which includes a container with at least one Raman probe positioned within. The Raman probe includes a Raman detection system configured to illuminate an area of a subject or a sample with a light source and to receive Raman scattered light energy from the area. The Raman probe also includes a proximity sensor system configured to measure the distance from the Raman probe to the area; and, optionally a fluorescent imaging system configured to detect fluorescence from the area. It also includes a sample holding system positioned within the container. The sample holding system is configured to position a sample and the at least one Raman probe relative to one another.

The present disclosure also describes a method of imaging a sample that includes introducing a sample into a container, optionally detecting fluorescent light from a first area of the surface, optionally guiding the Raman probe to the first area based on the detected fluorescent light, positioning the Raman probe at a target distance from the first area of the sample, wherein the positioning at the target distance is determined using a proximity sensor system. An area of a sample is exposed to a light beam from the Raman detection system, in which the light beam is scattered by a Raman agent associated with the area. The scattered light beam is referred to as a Raman scattered light energy. The Raman scattered light is detected using the Raman imaging device.

A method of imaging a sample is described that includes introducing a sample into a container. Fluorescent light is optionally detected from a first area of a surface. The Raman probe is optionally directed to the first area based on the detected fluorescent light and the sample positioned relative to the Raman probe at a distance from the area of the sample. Said distance is determined using a proximity sensor system. The area of the sample is exposed to a light beam from the Raman detection system, wherein the light beam is scattered by a Raman agent associated with the first area. The light beam that is scattered is referred to as a Raman scattered light energy. The Raman scattered light is detected using a Raman imaging device; and a normalized Raman date generated from the Raman scattered light based on the distance measured using the proximity sensor system.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 3A-3B illustrate embodiments of the wide-field fluorescent image guided Raman spectrometer.

Figure 1:
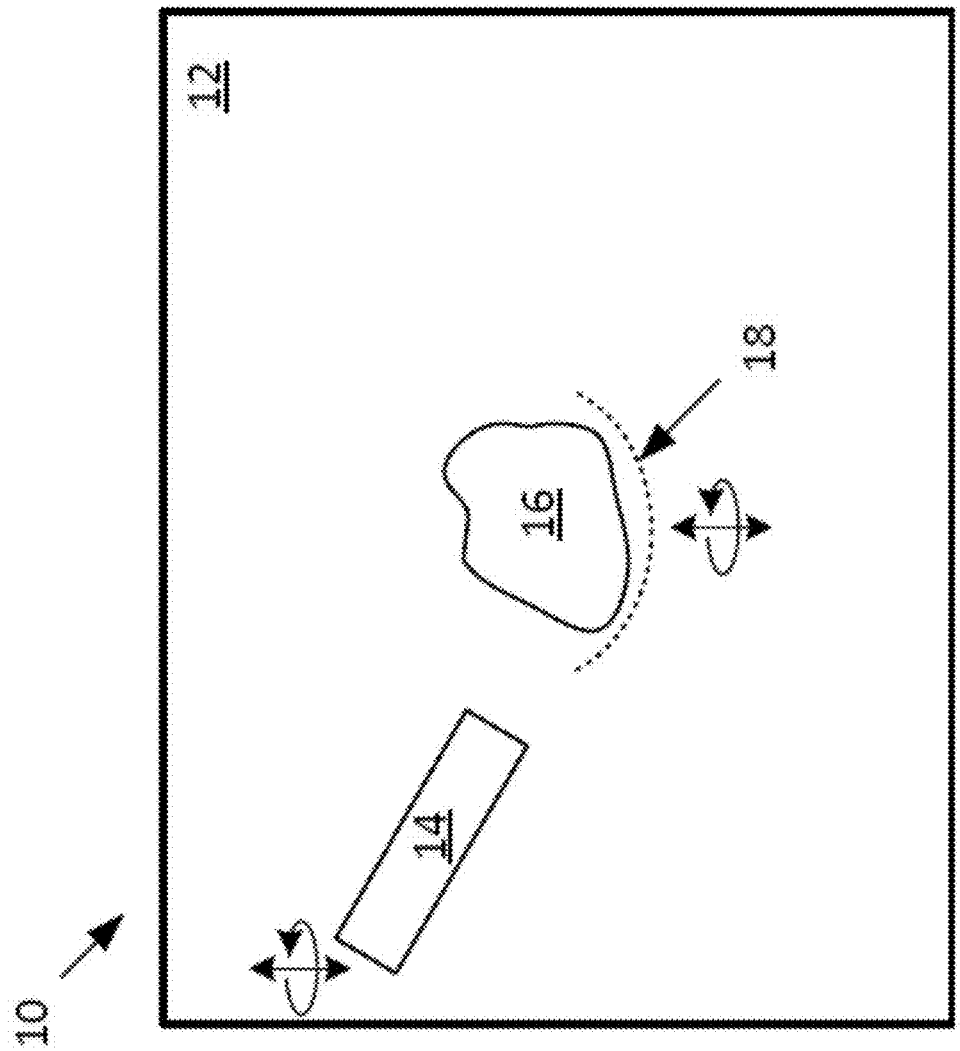
FIG. 1 illustrates an embodiment of the Raman topography system that includes a single Raman probe positioned in a container where an excised sample is held in place using a sample holding system.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biochemistry, biology, molecular biology, imaging, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "introduction" refers to exposing an excised sample (e.g., excised tissue) to an agent (or a compound, cell, or virus, including the agent, where the agent can be a Raman agent or fluorescent agent, for example). In an embodiment, the agent can be poured over the excised sample for a period of time so that the agent can associate with the target area and/or the excised sample can be disposed (e.g., submerged) into a solution for a period of time so that the agent can associate with the target area.

In accordance with the present disclosure, "a detectably effective amount" of the agent (e.g., a Raman agent such as a SERS nanoparticle) of the present disclosure is defined as an amount sufficient to yield an acceptable image after introduction of the agent to the excised sample using a Raman device (e.g., Raman probe) of the present disclosure. The detectably effective amount of the agent of the present disclosure can vary according to factors such as disease type, type of agent, and the like. Detectably effective amounts of the agent of the present disclosure can also vary according to instrument and digital processing related factors. Optimization of such factors is well within the level of skill in the art.

As used herein, the term "sample" includes tissue excised humans, mammals, and birds (e.g., mice, rats, pigs, cats, dogs, birds, and horses).

As used herein, the term "tissue" includes excised normal or tumor tissue during surgery/biopsy from various areas of the body including, but not limited to, breast, head and neck, skin, brain, and the like.

The term "Surface-Enhanced Raman Scattering (SERS)" refers to the increase in Raman scattering exhibited by certain molecules in proximity to certain metal surfaces. (see, U.S. Pat. No. 5,567,628) The SERS effect can be enhanced through combination with the resonance Raman effect. The surface-enhanced Raman scattering effect is even more intense if the frequency of the excitation light is in resonance with a major absorption band of the molecule being illuminated. In short, a significant increase in the intensity of Raman light scattering can be observed when molecules are brought into close proximity to (but not necessarily in contact with) certain metal surfaces. In an embodiment, the metal surfaces can be "roughened" or coated with minute metal particles. Metal colloids also show this signal enhancement effect. The increase in intensity can be on the order of several million-fold or more.

The term "reporter compound" can refer to a Raman-active label. The term "Raman-active label" can refer to a substance that produces a detectable Raman spectrum, which is distinguishable from the Raman spectra of other components present, when illuminated with a radiation of the proper wavelength.

As used herein, the term "Raman agent" refers to the compounds or structures of the present disclosure that are capable of serving as imaging agents either alone or in combination with attached molecules (e.g., antibodies, proteins, peptides, small organic molecules, aptamers, and the like).

Discussion

In accordance with the purpose(s) of the present disclosure, as embodied and broadly described herein, embodiments of the present disclosure, in one aspect, relate to Raman topography systems, methods of using the Raman topography system, and the like.

Embodiments of the present disclosure seek to improve, simplify, and more efficiently detected the presence and location of a disease (e.g., cancer, tumor) on an excised tissue, where the presence and location of the disease can be used to guide a surgeon regarding complete or incomplete removal of the disease in the patient from which the tissue was excised. The detection of the diseased tissue can be performed quickly during surgery and in close proximity to the surgery, which will improve outcomes.

An embodiment of the Raman topography system includes at least one Raman probe positioned within a container and a sample holding system positioned within the container, where the (or each when multiple probes are present) Raman probe is directed towards a sample in the sample holding system. In an embodiment, the sample holding system and the Raman probe relative are positioned relative to one another so that the Raman probe can capture an image of the surface of the sample. The Raman probe is positioned at a known and controllable target distance from a first area of the sample. An image can be obtained for the entire surface of the sample by obtaining multiple images using one or Raman probes and changed the relative position to image the entire sample surface or using enough Raman probes to image the entire surface without the need for moving the Raman probe and/or surface holding system. In this regard, the Raman probe and/or the sample holding system can be moved relative to one another to image the entire surface of the sample. Once the surface is imaged, the images can be used to provide a topographical map of the surface of the sample so the presence or absence a disease (e.g., cancer, tumor, cancerous tissue, pre-cancerous tissue, or tissue of interest) on the entire surface can be considered. For example, if the topographical map indicates that an area of the sample includes cancerous tissue, the surgeon can excise additional tissue from the patient at that time that corresponds to the position that the excised tissue showed cancerous tissue as still present in the patient, which will ensure that all of the cancerous tissue is removed in a single surgery.

In an embodiment, the container can include a "black box" that has dimensions to include the Raman probe(s), the excised sample, and the sample hold system. In addition, the container can include appropriate environmental controls for temperature, vacuum pumps, and the like as well as components to support the Raman probe(s), the sample holding system, and the like. In an embodiment, the container can be made of materials such as, but not limited to, plastic, fiberglass, or stainless steel.

In an embodiment, the Raman probe can include a Raman detection system, a proximity sensor system, and optionally, a fluorescent imaging system. Briefly, the Raman detection system can be configured to illuminate an area of the excised sample with a light source and to receive Raman scattered light energy from the area. In an embodiment, the proximity sensor system can be configured to measure the distance from the Raman probe to the area so that obtained signal can be maximized and to ensure that the images of each area of the sample are obtained at the same distance so that the obtained signals from different images can be meaningfully compared. In an embodiment, the fluorescent imaging system configured to detect fluorescence from the area, which allows for the Raman probe to be generally positioned relative to the excised sample. Additional details are provided herein.

In an embodiment, the sample holding system functions to position the excised sample in a manner so that the entire surface of the excised sample can be imaged using the Raman probe system. The sample holding system is configured to rotate the excised sample along each x-, y-, and z-axis. As mentioned, the sample holding system and the Raman imaging system can both be moved to position the sample at the target distance from the Raman probe. In addition, the sample holding system is configured to obscure a minimal amount of the surface of the excised sample so that an accurate topographical map can be obtained for the entire surface of the excised sample. In an embodiment, the sample holding system can include a rod in which the sample/tissue is pierced and the rod can rotate allowing for imaging of the entire sample. Alternatively, the sample/tissue could be suspended using a thread or suture material that is threaded through the tissue sample and rotated to allow for imaging of the entire sample. In another embodiment, magnets can be implemented to suspend the sample/tissue for imaging and induce a magnetic field that then rotates the sample/tissue for imaging.

In an embodiment, the excised sample can include excised tissue from a patient. The excised tissue can be from any area of the body and is typically a diseased tissue. The excised tissue also includes healthy tissue since one has to remove past the boundary of the diseased tissue to ensure that the diseased tissue is completely removed. As a result, determining the presence of diseased tissue on the surface of the excised tissue is an indication not all of the diseased tissue has been removed from the patient. If healthy tissue is on the entire surface of the excised tissue, then the likelihood that all of the diseased tissue has been removed is high. In an embodiment, the excised tissue can include excised pre-cancerous tissue, cancerous tissue, tumor tissue, biopsied tissue, and normal tissue. The excised tissue can range in size from about $mm^3$ to $cm^3$. As described in more detail herein, the excised tissue is exposed to agents (e.g., Raman agents, fluorescent agents, and the like) that can provide signals that can be measured that correspond to the presence or absence of the diseased tissue.

Figure 2:
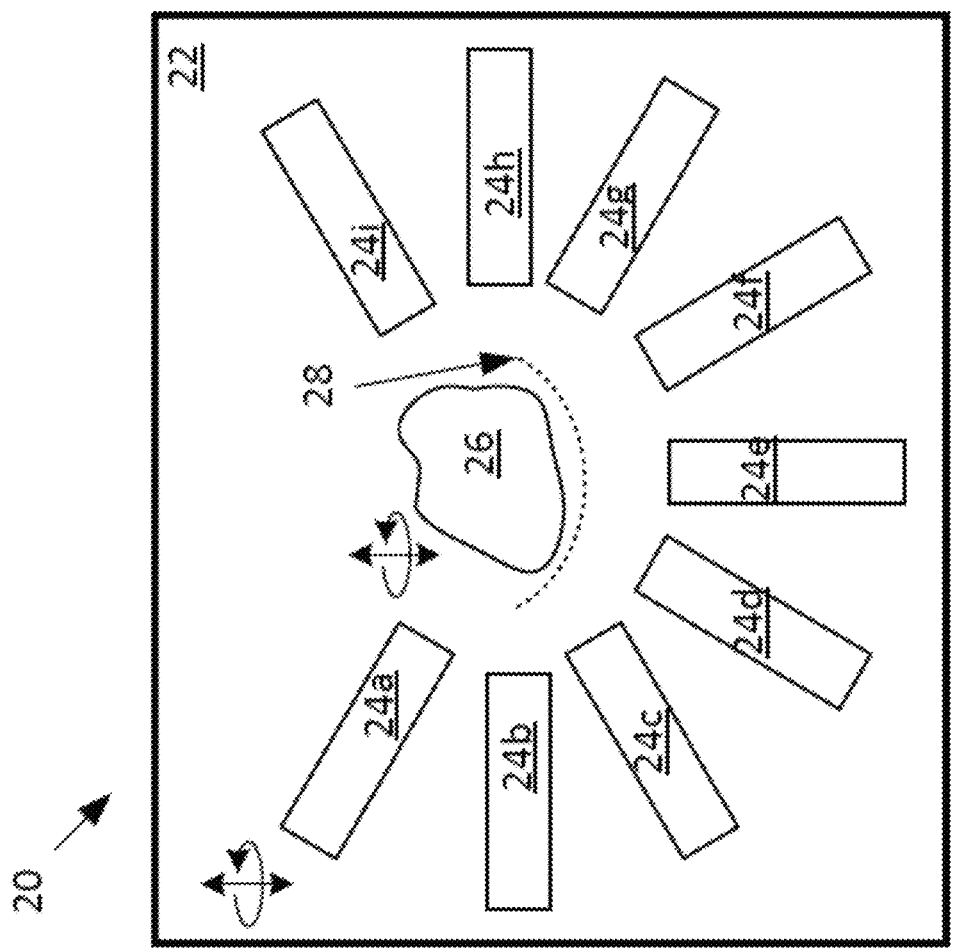
FIG. 2 illustrates an embodiment of the Raman topography system that includes a plurality of Raman probes positioned in a container where an excised sample is held in place using a sample holding system.

FIGS. 1 and 2 illustrate views embodiments of the present disclosure. FIG. 1 illustrates an embodiment of the Raman topography system 10 that includes a single Raman probe 14 positioned in a container 12 where an excised sample 16 is held in place using a sample holding system 18. The Raman probe 14 and/or the sample holding system 16 can be moved relative to one another so that an image can be obtained for the entire surface of the excised sample 16. The proximity sensor system of the Raman probe 14 can be used to position the Raman probe 14 at a target distance from the excised sample 16 by moving the Raman probe 14 and/or the sample holding system 18. A plurality of images can be obtained to construct a topographical map of the surface of the excised sample.

FIG. 2 illustrates an embodiment of the Raman topography system 20 that includes a plurality of Raman probes 24a-24i positioned in a container 22 where an excised sample 26 is held in place using a sample holding system 28. The Raman probes 24a-24i and/or the sample holding system 26 can be moved relative to one another so that an image can be obtained for the entire surface of the excised sample 26. The proximity sensor system of each of the Raman probes 24a-24i can be used to independently position each of the Raman probe 24a-24i at a target distance from the excised sample 26 by independently moving the Raman probe 24a-24i and/or the sample holding system 28. A plurality of images can be obtained to construct a topographical map of the surface of the excised sample.

Additional details regarding the Raman topography system are provided herein. At this point, the method of imaging the excised sample will be provided. An embodiment of the present disclosure includes a method of imaging a sample, for example, using the Raman topography system described herein. An excised sample is obtained and introduced to a container and suspected using a sample holding system. Prior to being introduced to the container, the excised sample is introduced to a solution (e.g., dipped into or the solution is poured over the sample) including the one or more targeting ligands. The targeting ligands have an affinity for the diseased tissue or components of the diseased tissue. In addition, the targeting ligands include a Raman agent and/or a fluorescent agent, which can be used to produce images of the surface and the topographical map of the surface.

Optionally, the Raman probe can be used to detect a fluorescent light from a first area of the excised sample. The Raman probe can be used to cause the production of the fluorescent light signal from the area. As mentioned herein, the Raman probe can direct a light onto the area and a fluorescent signal can be produced from a fluorescent agent associated with the area (e.g., a target fluorescent agent having an affinity for a target (e.g., cancerous cells or tissue, tumor)) or generated by the native tissue. The received fluorescent signal can be used to guiding the Raman probe to the first area of interest of the excised tissue based on the detected fluorescent light, where the detected fluorescent light is associated with the target. In other words, the fluorescent signal can be used to as a broad guide to the area of interest, and a more refined and detailed image can be accessed using scattered Raman light energy as discussed below.

Once the area of interest is determined, the Raman probe can be positioned at a target distance from the area of interest. The positioning at the target distance is determined using the proximity sensor system. As discussed herein, the target distance is used to maximize the detected scattered Raman light energy and/or normalize the distance from the area of interest. The target distance and the proximity provide are discussed in greater detail herein.

Once positioned at the target distance, the first area of the excised sample is exposed to a light beam from the Raman detection system. In general, the light beam is scattered by the Raman agent associated with the first area. The Raman scattered light energy can be detected. Additional details regarding the Raman detection system are provided herein.

This method can be repeated for each area of the surface of the excised sample. The method can use one or more Raman probes to obtain the images of the entire surface of the excised sample. Each image is obtained from the target distance. The Raman probe detects the Raman scattered light and this can be correlated to a position in the area so that a topographical map can be obtained for the area. As a result, a topographical map of the surface of the excised sample can be obtained. As discussed herein, the sample holding system and/or the Raman probe(s) can be moved to obtain images from the entire surface of the excised sample. There may be situations where the entire surface of the excised sample is not needed, and the method can be adapted to obtain images of the surface of interest of the excised sample.

In another embodiment of the present disclosure, the method of imaging a sample, for example, using the Raman topography system where the Raman probes are a fixed location. An excised sample is obtained and introduced to a container and suspected using a sample holding system. Prior to being introduced to the container, the excised sample can be processed in a similar manner as described above and herein. Optionally, the Raman probe can be used to detect a fluorescent light from a first area of the excised sample. The Raman probe can be used to cause the production of the fluorescent light signal from the area. As mentioned herein, the Raman probe can direct a light onto the area and a fluorescent signal can be produced from a fluorescent agent associated with the area (e.g., a target fluorescent agent having an affinity for a target (e.g., cancerous cells or tissue, tumor)) or generated by the native tissue. The received fluorescent signal can be used to direct the Raman probe to the first area of interest of the excised tissue based on the detected fluorescent light, where the detected fluorescent light is associated with the target. In other words, the fluorescent signal can be used to as a broad guide to the area of interest, and a more refined and detailed image can be accessed using scattered Raman light energy as discussed below.

Once the area of interest is determined, a distance from the Raman probe to the area of interest can be determined using the proximity sensor system. The determined distance can be used to normalize the Raman data using a predetermined calibration table or mathematical model. This is an alternative approach to the moving the Raman probe(s) to the target distance.

Subsequently, the first area of the excised sample is exposed to a light beam from the Raman detection system. In general, the light beam is scattered by the Raman agent associated with the first area. This method can be repeated for each area of the surface of the excised sample. The method can use one or more Raman probes to obtain the images of the entire surface of the excised sample. The Raman probe detects the Raman scattered light and this can be normalized and correlated to a position in the area so that a topographical map can be obtained for the area.

As discussed herein, the sample holding system and/or the Raman probe(s) can be moved to obtain images from the entire surface of the excised sample. There may be situations where the entire surface of the excised sample is not needed, and the method can be adapted to obtain images of the surface of interest of the excised sample.

Now having described the Raman topological system in general, additional details regarding the Raman probe and other components are now provided. In an embodiment, the Raman probe can be used in conjunction with one or more types of Raman agents, where each produce a detectably distinguishable Raman light scattering signal. In addition, the Raman detection system can excite each of the Raman agents with light and sensitively detect Raman scattered light energy signals emitted from each of the Raman agents. In particular, the Raman probe can be used in conjunction with Raman agents that target a specific disease to detect at the disease margins with greater sensitivity than what is currently used.

As discussed above, embodiments of the present disclosure can be advantageous in that an embodiment of the Raman probe can use a proximity sensing system to normalize the Raman signal to reduce the quadratic drop off associated with distance from sample surface. In addition, embodiments of the present disclosure can be advantageous because it can provide a dual modal fluorescence/Raman detection capability. Another embodiment can include the dual modal fluorescence/Raman detection capability and the proximity sensing system.

In an embodiment where the Raman probes are in a fixed position, the Raman data can be normalized to generate the topological map. Use of a fixed position for the Raman probe allows for a simple mechanical system that uses a computer to normalize the Raman data to adjust for the variation in distance of the Raman probe to the tissue surface.

In an embodiment, the Raman probe includes a Raman detection system and one or both of a fluorescent imaging system and a proximity sensor system. In an embodiment, the Raman detection system can be configured to illuminate an area of interest in the excised sample with a light source and to receive Raman scattered light energy from the area of interest of the excised sample, where the light energy is scattered by one or more Raman agents associated with a disease or condition. Additional details are described herein.

In an embodiment, the fluorescent imaging system is configured to detect fluorescence from the area of interest of the excised sample. In an embodiment, the fluorescent imaging system can include a wide-field fluorescent imager, which can be used to consider a large field of view that can be used to guide the user (e.g., a surgeon) to the area of interest of the excised sample. In an embodiment, the fluorescent imaging system can include the use of an excitation laser, a gradient index (GRIN) optics lens and a camera for wide field emitted light detection.

In an embodiment, a fluorescent agent can be used that can be conjugated with a targeting agent having an affinity for the target area (e.g., tissue, cell, tumor, cancerous tissue, and the like). Additional details regarding fluorescent agents are provided herein.

In an embodiment, the proximity sensor system is configured to measure the distance from the Raman probe to the area of interest of the excised sample. The distance from the Raman probe to the area of interest of the excised sample can play a role of the detection of the Raman scattered light energy. In addition, use of a uniform distance for measuring the Raman scattered light energy from different points on the sample should be done to generate a meaningful topological map of the total of the areas of interest of the excised sample. In particular, since there is a $1/r^2$ drop off of the Raman scattered light energy with working distance away from the excise tissue surface, use of the proximity sensor system (e.g., time of flight sensor (ST FlightSense™ technology) provides the ability to normalize acquired signals from multiple areas of interest of the excised tissue surface. In contrast, if the signals are acquired from different distances, the relative intensity of the signals can obscure the true nature of the excised tissue. In other words, use of signals acquired from different distance can generate more false positives or false negatives. Thus, use of the proximity sensor system can be used to measure the distance away from the excised tissue surface and renormalize the signal due to the quadratic response seen with varying working distances. As a result, the Raman probe including the proximity sensor system can be used to determine differences in spectral Raman intensity in real time and/or to generate a realistic topological map of the excised tissue being investigated or of interest.

In an embodiment, the proximity sensor system can include, but is not limited to, sensors found at ST microelectronics. In an embodiment, the proximity sensor can include SparkFun "Time of Flight" Range Finder®, a sensor board for the VL6180 distance sensor. Unlike most distance sensors that rely on reflected light intensity or reflected angles to determine range, the VL6180 uses a precise clock to measure the time it takes light to bounce back from a surface. As a result, the ToF Range Finder® and VL6180 can provide a more accurate measurement and is influenced by noise to a lesser degree.

The target distance can be the distance that one would like to position the probe from the surface of the area of the excised tissue to reduce the $1/r^2$ drop off and maximize the Raman signal. In an embodiment, the target distance can be about 0.001 to 50 mm or about 0.001 to 20 mm. In an embodiment, the target distance used for different areas should be about (e.g., ±11 to 10% or 5 to 10%) the same as each other or equal to each other.

In another embodiment, the proximity sensor system is used to measure the distance from the Raman probe to the surface of the tissue sample. The distance can then be used to normalize the received Raman scattered light energy (Raman data).

The Raman probe includes one or more channels down the length of the Raman probe. The components of the Raman detection system and one or both of a fluorescent imaging system and the proximity sensor system are positioned within one or more of the channels. In an embodiment, the Raman probe includes a single channel including all of the components. In an embodiment, the outside diameter of the Raman probe can be about 1 to 25 mm or about 20 mm. In an embodiment, the inside diameter of the Raman probe can be about 5 to 15 mm or about 10 mm. In an embodiment, the Raman probe can have a length of about 5 to 20 cm (not including the extended fiber bundle to be attached to the corresponding lasers and spectrometer). Additional details regarding the dimensions and configuration of the Raman probe are provided in the Examples and figures.

In an embodiment the light source is selected from one or more from the following group: a light emitting diode (LED), a laser, a diode laser, and a super luminescent laser diode (SLD). In an embodiment, the Raman probe includes a light source (e.g., a laser) or is adapted to direct a light source (e.g., uses a fiber to guide the light) that may be generated separately from the Raman probe, and a device or structure to receive or detect Raman scattered light energy (e.g., uses a fiber to collect light). In an embodiment, the Raman scattered light energy can then be measured by a device (e.g., a spectrometer/CCD).

Embodiments of the Raman probe can include a fiber bundle, one or more lenses for collimating a light beam (e.g., a laser at a wavelength that the Raman agents scatter the light) and for focusing the fluorescent light and/or Raman scattered light energy, and optionally filters for delivering and collecting the appropriate light signals. Other components can be part of the Raman probe or used in conjunction with the Raman probe (e.g., a Raman probe system) and these include a spectrometer and charge-coupled device (CCD) camera for collection and measurement of inelastically scattered light.

In an embodiment, the Raman detection system can include an optical fiber system to direct light derived from the light source to the area. In addition, the Raman detection system can be used to collect and direct the Raman scattered light energy to the Raman detection system.

In an embodiment, the Raman detection system includes an optic system (e.g., mirrors, lenses, and the like). In an embodiment, an optic system can be disposed between the optical fiber system and the sample to concentrate the light onto the sample. In addition, the optic system can be used to collect the Raman scattered light energy from the sample. In an embodiment, the optic system can capture and concentrate the collected Raman scattered light energy into the optical fiber system.

In an embodiment, the optical fiber system can include a single fiber to guide light derived from the light source to the area. In an embodiment, the optical fiber system can include a fiber bundle to guide Raman scattered light energy from the area to a Raman detection system. In an embodiment, a single mode fiber can be used to direct the light out of the Raman probe while one or more (e.g., 37 fibers) can be used to receive the light (e.g., scattered Raman light energy, fluorescence).

Optionally the Raman probe can include collection and measurement devices or instruments to collect and measure the scattered Raman light energy. In an embodiment the Raman probe can include one or more lenses to guide the light and the scattered Raman light energy, one or more mirrors to direct the laser light or scattered Raman light energy, and/or one or more filters to select certain wavelengths of light and/or scattered Raman light energy.

In an embodiment, a collimating lens can be used. In an embodiment, the collimating lens placement allows for a consistent Raman signal to be produced over a variety of working distances. Although exemplary working distances are described below, embodiments of the present disclosure are not limited to these distances and other reasonable distances for the particular application can be determined and used. In an embodiment, the Raman probe can have an illumination range of about 300 nm to 10 mm for light produced for Raman detection. In an embodiment, the Raman/Fluorescent probe can have an illumination range of about 300 nm to 10 mm for fluorescent detection.

In an embodiment, enabling software can display (in order to inform the user/physician) the relative signal strength of received signal (e.g., fluorescent and/or Raman signal) as well as the ratio signal strength (e.g., for embodiments including different types Raman agents).

In an embodiment, an ultrasound transducer array can be incorporated into the Raman probe. With an array of ultrasound transducers, photoacoustic or ultrasound imaging can be performed.

One of the principles by which embodiments of the present disclosure operate is based on the Raman Effect. When light is scattered from a molecule most photons are elastically scattered. However, a small fraction of light is scattered at optical frequencies different from and usually lower than the frequency of the incident photons. The process leading to this inelastic scatter is termed the Raman Effect. However, this effect is can be relatively weak, only producing one inelastically scattered photon for every 10 million elastically scattered photons.

In an embodiment, a surface enhanced Raman scattering (SERS) agents can be used. SERS is a plasmonic effect where small molecules adsorbed onto a nano-roughened noble metal surface, for example, experience a dramatic increase in the incident electromagnetic field resulting in several orders of magnitude higher Raman intensity. The increase in the Raman Effect allows embodiments of the present disclosure to detect pM concentrations of Raman agents with the Raman imaging device. The Raman agents can be selected so that they include unique Raman active molecules (that can be interchanged for multiplexing capabilities) adsorbed onto a metal core.

In an embodiment, the fluorescent and/or Raman agents can be conjugated to a disease targeting agent or ligand that has an affinity for and a binding potential to the diseased area as opposed to normal tissue. Once the agent has been conjugated to the appropriate disease targeting ligand or agent, the agent can be exposed (e.g., dipped into a solution or others soaked) to the excised tissue and the agent is given an appropriate amount of time to bind to the targeted disease (e.g., diseased tissue or cells or compounds associated with the disease). Subsequently, using the Raman probe, a light beam can be directed onto the area of interest (e.g., which may include the suspected diseased area) to detect fluorescent signal or the inelastic scattered energy (Raman scattering light energy) coming from disease targeted Raman agents (or the tissue).

As mentioned above, embodiments of the present disclosure include using Raman agents to locate and detect a signal from a diseased area of interest of the excised sample. In an embodiment, the Raman agents give a much more intense Raman signal than the intrinsic Raman scattering from the tissues themselves (e.g., about $10^7$ orders of magnitude greater) allowing the achievement of at least pM sensitivity.

As mentioned above, the Raman probe can be used to measure a signal, where the signal originated from a particular location. In an embodiment, the Raman probe, in conjunction with an analysis system (e.g., computer, software, etc., are interfaced with the Raman probe), is capable of creating an image of an examined area of a living host (e.g., colon), which is in contrast to just measuring a signal in a host. In addition, the Raman probe can examine multiple areas of the excised tissue surface and generate a topological map of the excised tissue.

A Raman image (e.g., the Raman scattered light energy) using embodiments of the present disclosure is different from a bulk signal in that the Raman image is a visual representation of signal as a function of location (e.g., a few millimeters, a centimeter or more).

In an embodiment, the Raman probe can be adjusted to adjust the distance from between it and the sample tissue surface. In an embodiment the Raman probe can be moved using an actuator or similar device or system. In another embodiment, the Raman probe is in a fixed position so that the distance between it and the sample tissue surface cannot be changed. But the Raman probe can be directed in that the Raman probe can be directed at a selected location on the sample tissue surface. In the alternative, the Raman probe cannot be adjusted or directed.

Raman Agents and Fluorescent Agents

The Raman agents can include Raman compounds and Raman nanoparticles. In an embodiment, the Raman compounds can include reporter compounds conjugated with one or more distinct targeting agents, both of which are described in more detail below. In an embodiment, the Raman nanoparticles include, but are not limited to, SERS nanoparticles, composite organic inorganic nanoparticles (COINS), Single walled nanotubes (SWNTs), methylene blue dye (other Raman active dyes), and the like. Each of the Raman nanoparticles can include targeting ligands (e.g., proteins) so that targeted areas (e.g., organs (e.g., colon, breast, and the like), and the like) can be imaged.

In an embodiment, the SERS nanoparticle includes, but is not limited to, a core, a reporter compound, and an encapsulant material. The encapsulant material covers and protects the core and reporter compounds. The reporter compounds are attached to the core. The core can be made of materials such as, but not limited to, copper, silver, gold, and combinations thereof, as well as of other metals or metalloids. Different types of SERS nanoparticles can be selected, where each SERS nanoparticle has a different Raman signature. Thus, the use of different SERS nanoparticles enables multiplexing. Additional details regarding this particular type of SERS nanoparticle is provided in WO 2006/073439, U.S. Pat. No. 6,514,767, and U.S. Patent Application No. 60/557,729, each of which are incorporated herein by reference as they pertain to the detailed description of each application or patent and as they relate to SERS nanoparticles and SACNs.

In an embodiment, one type of SERS nanoparticle includes Surface Enhanced Spectroscopy-Active Composite Nanoparticles (SACNs). SACNs and methods of making SACNs are described in WO 2006/073439, U.S. Pat. No. 6,514,767, and U.S. Patent Application No. 60/557,729, each of which is incorporated herein by reference as they pertain to the detailed description of each application or patent and as they relate to SACNs. Embodiments of the SACNs can include a SERS nanoparticle, a submonolayer, monolayer, or multilayer of reporter molecules in close proximity to the metal surface, and an encapsulating shell (e.g., a polymer, glass ($SiO_x$), or other dielectric material). In an embodiment, the reporter compound is disposed at the interface between the SERS nanoparticle and the encapsulant. In an embodiment, a SACN comprises (i) a metal nanoparticle core (e.g., Au or Ag), (ii) a Raman-active reporter (reporter compound), that gives a unique vibrational signature, and (iii) an $SiO_x$:encapsulant that "locks" the reporter molecules in place while also providing a highly compatible surface for subsequent immobilization of biomolecules. The glass coating can also stabilize the particles against aggregation and can prevent competitive adsorption of unwanted species. In an embodiment, the SERS nanoparticles are comprised of polymer coatings adjacent to the nanoparticle.

As used herein, the term "reporter compound" includes Raman-active compounds that produce a unique SERS signature in response to excitation by a laser. In certain embodiments, Raman-active organic compounds are polycyclic aromatic or heteroaromatic compounds. In an embodiment, the reporter compound can include, but is not limited to, 4-mercaptopyridine (4-MP); trans-4,4'bis (pyridyl)ethylene (BPE); quinolinethiol; 4,4'-dipyridyl, 1,4-phenyldiisocyanide; mercaptobenzamidazole; 4-cyanopyridine; 1',3,3,3',3'-hexamethylindotricarbocyanine iodide; 3,3'-diethyltiatricarbocyanine; malachite green isothiocyanate; bis-(pyridyl)acetylenes; Bodipy; TRIT (tetramethyl rhodamine isothiol); NBD (7-nitrobenz-2-oxa-1,3-diazole); Texas Red dye; phthalic acid; terephthalic acid; isophthalic acid; cresyl fast violet; cresyl blue violet; brilliant cresyl blue; para-aminobenzoic acid; erythrosine; biotin; digoxigenin; 5-carboxy-4',5'-dichloro-2',7'-dimethoxy fluorescein; 5-carboxy-2',4',5',7'-tetrachlorofluorescein; 5-carboxyfluorescein; 5-carboxy rhodamine; 6-carboxyrhodamine; 6-carboxyletramethyl amino phthalocyanines; azomethines; cyanines; xanthines; succinylfluoresceins; aminoacridine; fullerenes; organocyanides (e.g., isocyanide), methylene blue indigo carmine, and indocyanine green (ICG), and the like, and combinations thereof.

A COIN includes several fused or aggregated primary metal crystal particles with the Raman-active organic compounds (reporter compound) adsorbed on the surface, within the junctions of the primary particles, or embedded in the crystal lattice of the primary metal particles. The primary metal crystal particles are about 15 nm to 30 nm, while the fused or aggregated COIN is about 50 nm to about 200 nm. The primary metal crystal particle is made of materials such as, but not limited to, gold, silver, platinum copper aluminum, and the like. The Raman-active organic compound refers to an organic molecule that produces a unique SERS signature in response to excitation by a laser. Additional details regarding COINS are described in U.S. Patent Applications 20050142567, 20060234248, and 20070048746, each of which is incorporated herein by reference for the corresponding discussion.

COINs can also serve as Raman nanoparticles to provide imaging signals. The COINs can be functionalized so they have better solubility in blood and can target potential targets in a living subject. Multiple COINs can be used with other Raman nanoparticles in order to provide multiplexing of signals.

In an embodiment, the Raman agent can be incorporated (e.g., disposed inside and/or attached to the surface of) or encapsulated into a biological agent (e.g., a cell or a virus). In particular, the Raman agent can be incorporated into stem cells, t-cells, bacterial strains, Red blood cells, white blood cells, and the like. As the encapsulating virus, bacteria, or stem cell moves through the body or within an area, the Raman imaging system can be used to monitor/track the virus, bacteria, or cell. Studying cell motility and tracking its natural distribution in the body is an important biological process that can offer scientists important information on how to better design diagnostics and therapeutics. By using a stem cell, for instance, incorporating a Raman agent (e.g. Raman active dyes or Raman nanoparticles) one could use the Raman signal to monitor its localization within the body after it has been administered for therapy for instance. One could also study the homing effects that bacteria, viruses, t-cells, or even macrophages have on tumor sites if these cells were to be previously encapsulated with Raman agents (e.g. Raman dyes or Raman nanoparticles). One could essentially use their Raman active signal as a reporter to track where exactly these cellular entities have localized after administration.

In an embodiment, the Raman compounds can include a reporter compound as noted above conjugated to a targeting ligand, so that the Raman agent or compound can have an affinity for a targeting ligand.

In an embodiment, the Raman agent can include a targeting ligand that is a chemical or biological ligand or compound having an affinity for one or more targets (e.g., also referred to as a "specific target" or "targeted area"). In an embodiment, the targeting ligand can include, but is not limited to, a drug, a therapeutic agent, a radiological agent, a chemological agent, a small molecule drug, a biological agent (e.g., antibodies, peptides, proteins, apatamers, antigens, and the like) and combinations thereof, that has an affinity for a target or a related biological event corresponding to the target (e.g., biomarkers). It should be noted that Raman agent modified with conjugation to other molecules (e.g., antibodies, proteins, peptides, apatamers, small molecules, and the like) in order to target the Raman agent to a particular molecular target are intended to be covered by embodiments of the present disclosure. For example, a Raman agent can be modified with a peptide so that it can target new blood vessels in tumors or a chemical associated with a specific cancer, tumor, or precancerous tissue. In an embodiment, the targeting ligand can have an affinity for a target such as cancer, tumor, precancerous cells or tissue, atherosclerosis, fibrosis. In another embodiment, the targeting ligand can be used for trafficking (where the Raman agent is incorporated into viruses or cells (e.g., stem cells, t-cells, Red blood cells, white blood cells, and the like)) to look at distribution in the body.

In an embodiment, the device does not necessarily need to use a "Raman agent", but can also utilize the intrinsic (or natural) Raman signal of the tissue itself or it can use contrast agents (such as fluorophores).

In an embodiment, the fluorescent agent can include fluorescent particle or dyes. In an embodiment, the fluorescent agent can include, but are not limited to, indocyanine green, methylene blue, and fluorescein or FITC.

In an embodiment, Raman agent and/or the fluorescent agent can be conjugated with one or more targeting agents (e.g., disease targeting compounds or ligands). The Raman agent and/or the fluorescent agent can then sensitively and specifically bind to the cells, proteins, and the like, related to the disease or condition of interest and their localization can be detected using the Raman probe.

EXAMPLES

Now having described the embodiments of the present disclosure, in general, the example describes some additional embodiments of the present disclosure. While embodiments of the present disclosure are described in connection with the example and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Raman Probe for Topographical System

An embodiment of the Raman probe includes a proximity sensor and a fluorescence wide field imaging component, where the fluorescence wide field imaging component offers the ability for wide field fluorescence imaging to help guide a Raman probe and the proximity sensor can position the Raman probe the desired distance from the excised tissue. Example configurations are shown in FIGS. 3A-3B.

As mentioned above, the Raman probe incorporates a feature that allows the probe to correct for varying distances away from the excised tissue. The sensor is meant to measure the distance away from the excised tissue and renormalize the signal due to the quadratic response seen with varying working distances, which allows determining differences in spectral Raman intensity in real time. The wide field fluorescence component was integrated into the handheld design, creating a multimodal option during clinical use. The wide field fluorescence component was integrated into the handheld design, creating a multimodal option during clinical use. This large field of view is meant to generally guide the Raman probe, then the user can switch to the Raman point detection scheme in order to acquire multiplexed molecular information about the tumor margins.

Example 2

Topographical Imaging Strategy

Figure 4:
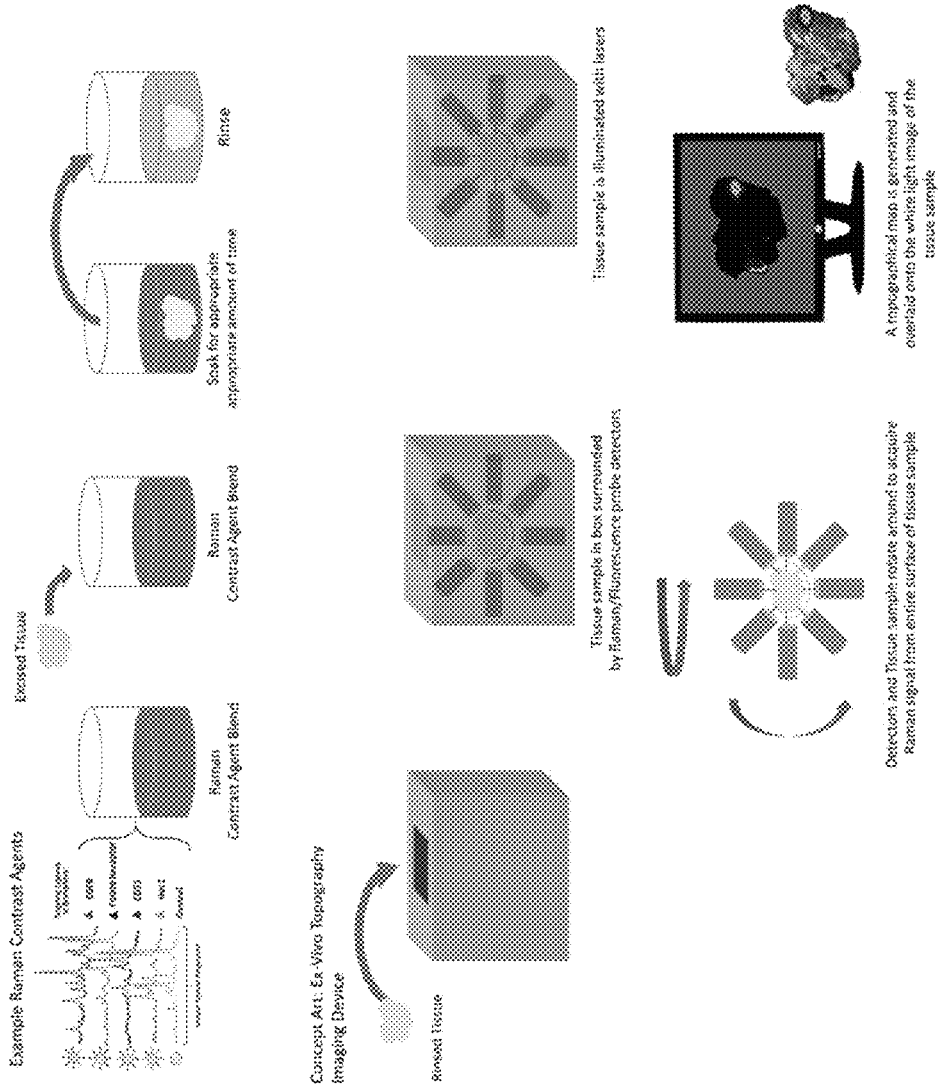
FIG. 4 is a schematic drawing depicting an example strategy for imaging tissue samples with the external topographical imaging device.

This strategy is intended to provide clinicians/surgeons with fast molecular imaging information about an excised tissue sample that can provide actionable information. The excised tissue sample can be taken from the patient and immediately soaked in a blend of Raman/Fluorescent contrast agents that have been conjugated with a disease targeting ligand (FIG. 4). After soaking, the tissue is then rinsed and immediately put into an ex-vivo topography imaging device where either a single detector or an array of detectors scans the entire surface of the tissue to acquire optical signal (Fluorescence or Raman). These optical signals are then post-processed to generate a topographical map of the surface of the tissue sample. The intensity map generated can be overlaid onto the tissue to help guide the clinicians/surgeons to take further action (FIG. 4).

FIG. 4 is a schematic drawing depicting the strategy for imaging tissue samples with the disclosed external topographical imaging device. The scheme involves taking an excised tissue sample soaking it in a blend of Raman contrast agents that have various targeting ligands conjugated to them. The figure shows some example targeting ligands for breast cancer as an example, however we are not limited to these specific targeting ligands. After soaking and rinsing, the tissue is inserted into the topography imaging device. The tissue is illuminated with lasers and the detectors and tissue rotate accordingly to acquire a full surface map of the entire tissue. The signals are then processed to generate an intensity map of the entire tissue surface. The topographical map is then overlaid on a three dimensional white light photo of the tissue sample to reveal where the signal was originally generated on the tissue.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding based on numerical value and the measurement techniques. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A method of imaging a sample, comprising:
   a) introducing a sample into a container of a Raman topography system, the system comprising:
      a container;
      at least one Raman probe positioned within the container, wherein the Raman probe includes:
         a Raman detection system, wherein the Raman detection system is configured to illuminate an area of a subject or a sample with a light source and to receive Raman scattered light energy from the area;
         a proximity sensor system configured to measure a distance from the Raman probe to the area;
   b) positioning the Raman probe at a target distance from a first area of the sample, wherein the positioning at the target distance is determined using a proximity sensor system configured to measure the distance from the Raman probe to the area;
   c) exposing the first area of the sample to a light beam from the Raman detection system, wherein the light beam is scattered by a Raman agent associated with the first area, wherein the light beam that is scattered is referred to as a Raman scattered light energy;
   d) detecting the Raman scattered light using a Raman imaging device;
   acquiring the Raman scattered light energy from the first area and each of the plurality of areas; and
   forming a topological map of the surface of the sample from the acquired Raman scattered light energy from the first area and each of the plurality of areas.

2. The method of claim 1, further comprising: repeating steps b) to f) b) to d) for a plurality of areas, where each of the plurality of areas is a different area of the subject.

3. The method of claim 1, wherein the at least one Raman probe includes a plurality of Raman probes, wherein steps b) to d) are performed for each Raman probe.

4. The method of claim 1, wherein the acquiring of each of the Raman signals occurs while rotating the sample, wherein the acquiring of each of the Raman signals occurs by moving the at least one Raman probe about the sample, or a combination thereof.

5. The method of claim 1, wherein one or more Raman contrast agents with varying targeting ligands are introduced to a surface of the sample.

6. The method of claim 5, wherein the sample is disposed in a solution including the one or more Raman contrast agents with or without targeting ligands.

7. The method of claim 1, further comprising one or both of:
a fluorescent imaging system configured to detect fluorescence from the area; and
a sample holding system positioned within the container, wherein the sample holding system is configured to position a sample and the at least one Raman probe relative to one another.

8. The method of claim 1, further comprising detecting fluorescent light from a first area of a surface, wherein the detecting occurs after step a).

9. The method of claim 8, further comprising guiding the Raman probe to the first area based on the detected fluorescent light.

10. The method of claim 1, wherein at least one Raman probe is positioned at a target distance from an area of the sample, wherein the target distance is determined and corrected by the proximity sensor system.

11. The method of claim 10, wherein the at least one Raman probe includes a plurality of Raman probes, wherein each Raman probe is positioned the target distance from the sample and each directed to a different area of the sample.

12. The method of claim 1, wherein the sample holding system and the at least one Raman probe are configured to be moved relative to one another so that the at least one Raman probe is positioned the target distance from a second area of the sample.

13. The method of claim 12, wherein the at least one Raman probe is mounted in a fixed position, wherein at least one Raman probe has an absolute working distance to the sample that varies as the sample is moved, wherein the Raman data is normalized according to a predetermined calibration table or mathematical model based on measurements using the proximity sensor system.

14. The method of claim 1, wherein the Raman signal is acquired while rotating the sample, wherein the Raman signal is acquired by moving the at least one Raman probe about the sample, or a combination of both.

15. The method of claim 1, wherein one or more of the Raman probes acquire Raman signal from around an entire area of the sample to form a topographical map of the surface of the sample.

16. A method of imaging a sample, comprising:
a) introducing a sample into a container of a Raman topography system, the system comprising:
a container;
at least one Raman probe positioned within the container, wherein the Raman probe includes:
a Raman detection system, wherein the Raman detection system is configured to illuminate an area of a subject or a sample with a light source and to receive Raman scattered light energy from the area;
a proximity sensor system configured to measure a distance from the Raman probe to the area;
b) positioning the sample relative to the Raman probe at a distance from a first area of the sample, wherein the distance is determined using the proximity sensor system;
c) exposing the first area of the sample to a light beam from the Raman detection system, wherein the light beam is scattered by a Raman agent associated with the first area, wherein the light beam that is scattered is referred to as a Raman scattered light energy;
d) detecting the Raman scattered light using a Raman imaging device; and
e) generating normalized Raman data from the Raman scattered light based on the distance measured using the proximity sensor system.

17. The method of claim 16, further comprising: repeating steps b) to d) for a plurality of areas, where each of the plurality of areas are different areas of the subject.

18. The method of claim 16, wherein the at least one Raman probe includes a plurality of Raman probes, wherein steps b) to d) are performed for each Raman probe.

19. The method of claim 16, wherein each of the Raman signals is acquired while rotating the sample, wherein each of the Raman signals is acquired by moving the at least one Raman probe about the sample, or a combination thereof.

20. The method of claim 16, wherein the area is a plurality of areas, and further comprising:
acquiring the Raman scattered light energy from the each of the plurality of areas; and
forming a topological map of the surface of the sample from the Raman data from each of the plurality of areas.

21. The method of claim 16, wherein one or more Raman contrast agents with varying targeting ligands are introduced to the surface of the sample or wherein the sample is disposed in a solution including the one or more Raman contrast agents with or without targeting ligands.

22. The method of claim 16, further comprising one or both of:
detecting fluorescent light from a first area of the surface; and
directing the Raman probe to the first area based on the detected fluorescent light.

23. The method of claim 16, further comprising detecting fluorescent light from a first area of the surface, wherein the detecting occurs after step a).

24. The method of claim 16, further comprising directing the Raman probe to the first area based on the detected fluorescent light, wherein the detecting occurs after step a).

* * * * *